United States Patent [19]

Pacey et al.

[11] Patent Number: 4,711,853
[45] Date of Patent: Dec. 8, 1987

[54] METHOD OF DETECTING POTASSIUM IONS USING TRIFLUOROMETHYL-SUBSTITUTED CHROMOGENIC CROWN ETHERS

[75] Inventors: Gilbert E. Pacey, Oxford, Ohio; Bernard P. Bubnis, Reston, Va.

[73] Assignee: The President and Trustees of the Miami University, Oxford, Ohio

[21] Appl. No.: 810,855

[22] Filed: Dec. 18, 1985

Related U.S. Application Data

[60] Continuation-in-part of Ser. No. 559,478, Dec. 8, 1983, abandoned, which is a division of Ser. No. 386,066, Jun. 7, 1982, Pat. No. 4,436,923.

[51] Int. Cl.[4] ................... G01N 21/75; G01N 33/50
[52] U.S. Cl. .............................. 436/74; 436/79; 436/164; 436/178
[58] Field of Search ............ 436/74, 79, 164, 178; 250/373; 252/193; 356/36, 433, 434, 435

[56] References Cited

U.S. PATENT DOCUMENTS 4,436,923 3/1984 Pacey et al. ............ 436/74 X

OTHER PUBLICATIONS

Takagi, M., Nakamura, H., Uneo, K., A Novel Colorimetric Reagent for Potassium Based on Crown Ether Complex Formation, *Anal. Lett.*, 1977, 10, 1115.
G. E. Pacey & B. P. Bubnis, A New Chromogenic Crown Ether 4"-Cyano-2",6"-Dinitro-4'-Aminobenzo-15-Crown-5 as an Alkali Metal Extraction Reagent, *Analytical Letters*, 13(A12), 1085–1091 (1980).
Naka-ura, H., Takagi, M., Uneo, K., Complexation and Extraction of Alkali Metal Ions by 4'-Picrylaminobenzo-18-Crown-6 Derivatives, *Anal. Chem.*, 1980, 52, 1668.
Nakamura, H., Takagi, M., Uneo, K., Photometric Reagents and Alkali Metal Ions, Based on Crown-Ether Complex Formation-III, 4'-Picrylaminobenzo-15-Crown-5 Derivatives, *Talanta*, 1978, 26, 921.
Pacey et al, Analyst, vol. 106, pp. 636–640, Jun. 1981.

*Primary Examiner*—Barry S. Richman
*Assistant Examiner*—Robert J. Hill, Jr.
*Attorney, Agent, or Firm*—Marshall, O'Toole, Gerstein, Murray & Bicknell

[57] ABSTRACT

Two novel trifluoromethyl-substituted chromogenic crown ethers are disclosed, 4'-(2",6"-dinitro-4"-trifluoromethylphenyl) aminobenzo-15-crown-5 and 4'-(2",4"-dinitro-6"-trifluoromethylphenyl) aminobenzo-15-crown 5. These compounds are useful as reagents for the extraction and spectrophotometric determination of potassium in the presence of sodium. Reagent solutions of these compounds and methods of utilizing the reagents for the analysis of potassium are disclosed and claimed.

17 Claims, 3 Drawing Figures

METHOD OF DETECTING POTASSIUM IONS USING TRIFLUOROMETHYL-SUBSTITUTED CHROMOGENIC CROWN ETHERS

This is a continuation-in-part of application Ser. No. 559,478 filed Dec. 8, 1983, now abandoned which is a division of application Ser. No. 386,066 filed June 7, 1982, now U.S. Pat. No. 4,436,923.

BACKGROUND OF THE INVENTION

The present invention relates to reagent solutions of certain chromogenic crown ethers and to methods of using these reagent solutions for the extraction and spectrophotometric determination of potassium. The crown ether compounds which can be employed in the reagents have the structural formula:

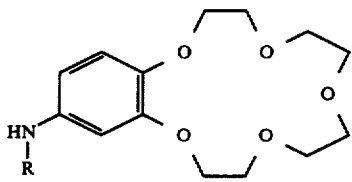

where R is taken from the group consisting of

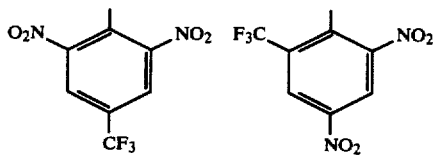

These crown ethers are systematically named 4'-(2",4"-dinitro-6"-trifluoromethyl-phenyl) aminobenzo-15-crown-5 and 4'-2",6"-dinitro-4"-trifluoromethylphenyl-)aminobenzo-15-crown-5, respectively.

Selective reagents which permit the isolation of a particular ion or ions from a complex matrix are of economic interest. In particular, with respect to the potassium and sodium ions which are present in many biological systems, a reagent having the ability to selectively (and quantitatively) extract one of these ions in the presence of the other would be of interest in biochemical assays.

The ability of crown ethers to selectively extract alkali and alkaline earth metal ions has been recognized in the art [Pedersen, C. J., *J. Am. Chem. Soc.*, 1967, 89, 7017]. Nonetheless, there has been little successful work in utilizing these compounds in analytical determinations until quite recently.

Of particular interest to the background of the present invention, is the description of the synthesis of a chromogenic crown like compound, 4'-picrylaminobenzo-15-crown-5, which was reported to be a selective extractant for potassium ions (10–800 p.p.m.) in the presence of sodium ions (2300 p.p.m.) [Takagi, M., Nakamura, H., and Ueno, K., *Anal. Lett.*, 1977, 10, 1115]. Unlike the case with the reagents of the present invention, however, the 4'-picrylamino-benzo-15-crown-5 reagent suffers both from a poor extraction efficiency and from spectral overlap of its protonated (HL) and deprotonated (ML) species. That is to say, the reagent can be used to extract K+ from solution by forming a complex of the form.

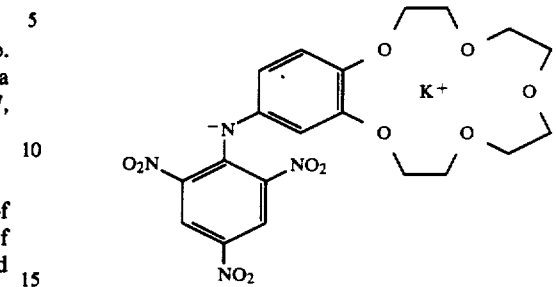

This (ML) compound, however, has a considerable spectral overlap with the unreacted reagent precursor (HL) compound.

Moreover, this picryl crown ether reagent does not readily quantitatively extract K+ in the presence of Na+. These same workers have reported efforts to improve the extraction efficiency of these reagent materials by adding bromo and nitro groups in the 5'position [Nakamura, H., et al, *Talanta*, 1978, 26, 921; Nakamura, H., et al, *Anal. Chem.*, 1980, 52, 1668].

SUMMARY

The present invention provides novel chromogenic crown ether reagents which can be used for the analytical detection of potassium. Both species of the novel reagent exhibit good extraction efficiencies and large differences in the value of the λ max and molar absorptivity between the complexed (ML) and uncomplexed (HL) species.

Both compounds are resistant to the influence of sodium ion on the determination. Experimental data indicates a linear range of 5 to 700 p.p.m. in the presence of as much as 3000 p.p.m. of sodium ion. The reagents are sensitive to rubidium ion at a concentration of 1000 p.p.m. As rubidium has a low natural occurrence, this should not be a problem in real samples.

DESCRIPTION OF THE INVENTION

The compounds of the present invention are dinitro-trifluoromethylphenyl-aminobenzo-15-crown-5 ethers, viz, 4'-(2",6"-dinitro-4"-trifluoromethylphenyl) amino-benzo-15-crown-5 (4TF) and 4'-(2",4"-dinitro-6"-trifluoromethylphenyl) aminobenzo-15-crown-5 (6TF).

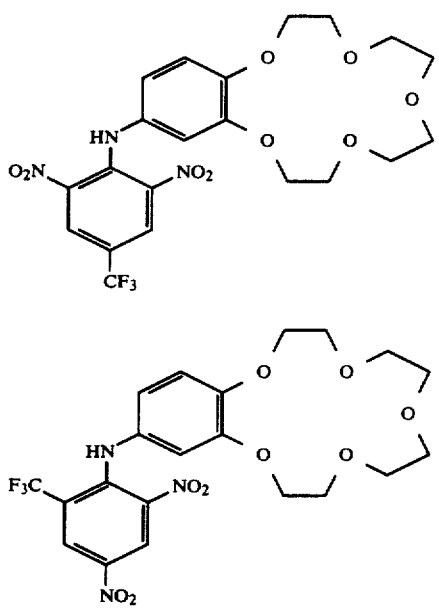

Figure 1:
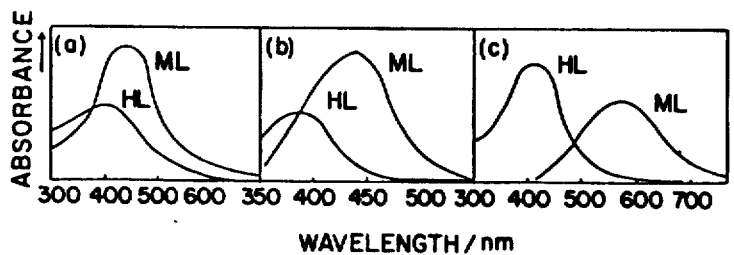
FIG. 1 is the ultraviolet-visible spectra of protonated (HL) and deprotonated complexed (ML) crown ethers: (a) 4'-picryl-aminobenzo-15-crown-5, $2\times10^{-4}$M in 10% dioxan-water; (b) 4'-(2",4"-dinitro-6"-trifluoromethylphenyl) aminobenzo-15-crown-5, $2\times10^{-4}$M in 40% acetonitrile-water; and (c) 4'-(2",6"dinitro-4"-trifluoromethylphenyl) aminobenzo-15-crown-5, $2\times10^{31}$ 4M in 40% acetonitrile-water.

The aqueous spectra of 4TF, 6TF, and for reference purposes, 4'-picrylaminobenzo-15-crown-5, in their protonated (uncomplexed) forms (HL) and in their dissociated (complexed) forms (ML) are shown in FIG. 1. The maximum absorptions and the molar absorptivities for the reagent species of FIG. 1 are shown in Table 1.

TABLE 1

WAVELENGTH MAXIMA AND MOLAR ABSORPTIVITIES FOR CHROMOGENIC CROWN ETHERS

| Reagent | Species | $\epsilon H_2O/$ 1 mol$^{-1}$ cm$^{-1}$** | $\lambda$max.$H_2O/$ nm | $\Delta\lambda$max./nm |
|---|---|---|---|---|
| 4'-Picrylamino- benzyl-15- crown-5 | HL | 13000 | 390 | 55 |
|  | ML* | 20000 | 445 |  |
| 4TF | HL | 6400 | 425 | 150 |
|  | ML* | 4400 | 585 |  |
| 6TF | HL | 13250 | 380 | 80 |
|  | ML* | 20800 | 460 |  |

*Depending on the alkali metal cation complexed in the crown cavity, the complexed form may be either ML or ML.HL.
**Molar absorptivity in water solvent expressed as wave numbers (cm$^{-1}$).

A significant feature is the decrease in spectral overlap between the HL and ML species for both 4TF and 6TF. In contrast, the overlap between the HL and ML species with 4'-picrylaminobenzyl-15-crown-5 is so great that the ML species had to be determined at a wavelength where, according to molar absorptivities, considerably less than maximum absorption occurs (20,000 versus 5000 l mol$^{-1}$ cm$^{-1}$).

Of the two compounds, 6TF is superior in terms of extraction efficiency and is capable of extracting 5 to 700 p.p.m. of potassium ions in the presence of 3000 p.p.m. of sodium ions. The 4TF compound, although somewhat inferior to the 6TF reagent in both spectral properties and extraction efficiencies, is clearly superior to the tested prior art compound.

Both 4TF and 6TF may be prepared by reacting 4'-aminobenzo-15-crown-5 with either 1-chloro-2, 6-dinitro-4-trifluoromethylbenzene or 1-chloro-4, 6-dinitro-2-trifluoromethylbenzene in organic solvent in the presence of a base, e.g., sodium bicarbonate. The resultant products (yields 60%) comprise dark orange powders, having melting points of 171° C. (4TF) and 165° C. (6TF).

Both the 4TF and 6TF crown ethers are soluble in a variety of organic solvents. Because of the proposed use of the compounds as reagents for spectrophotometric determinations, the preferred solvent is chloroform. Of the materials tested, chloroform alone works sufficiently well, in terms of the acid-base character of the crown ether, to be used in analytical determinations. Both toluene and dichloromethane were unsatisfactory because their background blanks were too large, owing to the complicated equilibrium established between the aqueous and non-aqueous acid-base chemistry of the chromogenic crown ether. Although the concentration of the crown ether may vary, it is preferred to employ reagent solutions in the range $1 \times 10^{-4}$ to $1 \times 10^{-2}$ molar, most preferably $2 \times 10^{-3}$ molar.

The extractions are performed by mixing an aqueous phase containing the dissolved cation with the organic reagent solution. In view of the fact that the two phases are immiscible, it is desirable to shake or otherwise agitate the twophase mixture to ensure that the extraction proceeds. For the same reason, it is preferred to use approximately equal volumes of organic and aqueous solutions. It was found that 5 minutes of agitation resulted in the extraction of approximately 80% of material with good precision. Therefore the results reported herein are based on a 5-minute extraction time. Other time constants could also be used.

The pH of the system was found to be critical as the amine proton on the 6TF and 4TF crown ether must dissociate in the aqueous phase before complexation and remain dissociated during and after the phase transfer. A basic buffer must be employed—e.g., a water-soluble amine or an inorganic base. For extractions utilizing the 6TF reagent, the pH of the aqueous phase after extraction should be greater than 9.5, and optimally between 9.52 and 10.22, the respective values of $pK_a'$ and $pK_a$ for the 6TF compound. At the low end of this pH range, color change is observed, but the change represents a mixture of the protonated (380 nm) and deprotonated, complexed (460 nm) spectra. The maximum of the peak shifts in the direction of the desired 460 nm $\lambda_{max}$ with increasing $pK_a$ of the buffer. Thus a pH of greater than 10 is desirable. Overly high pH (>11), however, can result in sample turbidity and should be avoided.

If an amine is used as the basic buffer, it can be incorporated in the organic reagent solution. By way of example, a preferred reagent composition can be prepared by dissolving 1.01 g of 6TF [$2 \times 10^{-3}$ moles] and 101 g of triethylamine (TEA) [1 mole] in 1 liter of chloroform. When a quantity of the above reagent is mixed with an equal volume of an aqueous, potassium-ion-containing solution, satisfactory analytical results are obtained.

Amines which can be employed as basic buffers include:

| Compound | $pK_a$ |
|---|---|
| Tri-i-butylamine | 10.42 |
| Triethylenediamine | 10.45 |
| Isopropylamine | 10.63 |
| Tripropylamine | 10.70 |
| Triethylamine | 10.72 |
| Dimethylamine | 10.77 |
| Di-n-propylamine | 10.91 |

| Compound | pK$_a$ |
| --- | --- |
| Diethylamine | 10.93 |

Because amines are soluble in the organic solvent, only a small amount reaches the aqueous phase where complexation occurs. (Hence the use of the 1 molar solution of TEA in the preferred reagent, supra.). Thus, the solubility of the amine in water is an important parameter. Any basic nitrogen-containing material satisfying these solubility and dissociation requirements can be employed. However, care should be taken not to utilize a material which will react with constituents of the sample.

Inorganic bases may also be used to adjust the pH of the aqueous sample. Of course, the base utilized should not dissociate to form an ion to which the reagent is sensitive (i.e., potassium and rubidium compounds should not be used; sodium ion concentrations up to about 2000 p.p.m. can be tolerated). The preferred inorganic bases are LiOH or CsOH. Although these organic hydroxides can be used alone, use of a buffer comprising the salt of a strong base and a weak acid in conjunction with the inorganic hydroxide is preferred. Suitable buffers which were tested and found satisfactory include:

50 ml 0.5M NaHCO$_3$ + 10.7 ml 0.1M LiOH; and
50 ml 0.5M Borax + 18.3 ml 0.1M LiOH.

Extraction constants were determined as described on page 309 in *Anal. Chim. Acta,* 1982, 139, 307–313. Comparison of pK$_{ex}$ values using the triethylamine, tripropylamine, and LiOH/borax buffers were determined. Using aqueous solutions containing 100 p.p.m. K$^+$ the following pK$_{ex}$ were calculated: 7.5 triethylamine; 7.9 tripropylamine; and 7.6 LiOH/borax.

After extraction, the organic and aqueous phases are permitted to separate, and the aqueous phase discarded. The organic phase containing entrapped potassium ion may be analyzed directly by spectrophotometric means utilizing a spectrophotometer which is responsive to ultraviolet-visible light having a wavelength in the range 300 to 700 nm. If the preferred concentration level of reagent solution is employed, however (2×10$^{-3}$M), it is generally desirable to further dilute the sample with CHCl$_3$/TEA(1M) prior to analysis as an aid to spectral resolution. A dilution of 1 ml–10 ml is preferred (2×20$^{-4}$M, based on the original (HL) ether).

Spectrophotometric measurements were carried out using a Hewlett-Packard 8450A reversed optics spectrophotometer with 10-mm glass cells. The pH measurements were carried out using a Corning, Model 12, pH meter. Characterization of the new organic compounds was accomplished using a JEOL nuclear magnetic resonance spectrometer and a PerkinElmer 180 infrared spectrophotometer. All elemental analyses were performed externally by Galbraith Laboratory.

EXAMPLE I

Synthesis of 4'-(2",6"-dinitro-4"-trifluoromethylphenyl) aminobenzo-15-crown-5

4"nitrobenzo-15-crown-5 was prepared by nitrating benzo-15-crown-5 in accordance with the procedure of Ungaro et al [Ungaro, R., El Hag, R., and Smid, J., *J. Am. Chem. Soc.,* 1976, 98, 5198]. The nitro group was catalytically reduced with hydrogen at 30 psi in freshly distilled dimethylformamide (DMF) in the presence of 10% Pd/C (palladium on carbon), forming 4'-aminobenzo-15-crown-5.

A mixture of the aminobenzo compound (3.9 g; 0.0137 mol), 1-chloro-2,6-dinitro-4-trifluoromethylbenzene (3.7 g; 0.0137 mol) and sodium bicarbonate (1.15 g; 0.0137 mol) was refluxed for 5 hours in 200 ml of absolute methanol. The mixture was cooled and filtered and the methanol was removed using a rotary evaporator. The residue was dissolved in isopropanol, and an equal volume of light petroleum (boiling range 30°–60° C.) was added in order to precipitate the impurities. The isopropanol-light petroleum mixed solvent was filtered and evaporated to give the chromogenic crown ether 4TF as a dark orange powder (melting point 171° C., yield 60%). Calculated for C$_{20}$H$_{22}$N$_3$O$_9$F$_3$: C, 48.74; H, 4.92; N, 8.12; and F, 11.02%. Found: C, 48.51; H, 4.41; N, 7.93; and F, 11.06%.

EXAMPLE II

Synthesis of 4'-(2",4"-dinitro-6"-trifluoromethylphenyl) aminobenzo-15-crown-5

4'aminobenzo-15-crown-5 was prepared in accordance with the procedure of Example I. A mixture of the aminobenzo compound (3.9 g; 0.0137 mol), 1-chloro-2,4-dinitro-6-trifluoromethylbenzene (3.7 g; 0.0137 mol) and sodium bicarbonate (1.15 g; 0.0137 mol) was refluxed for 5 hours in 200 ml of absolute methanol. The mixture was cooled and filtered, and the methanol was removed using a rotary evaporator. The residue was dissolved in isopropanol, and an equal volume of light petroleum (boiling range 30°–60° C.) was added in order to precipitate the impurities. The isopropanol-light petroleum mixed solvent was filtered and evaporated to give the chromogenic crown ether 6TF as a dark orange powder (melting point 165° C.), yield 60%). Calculated for C$_{20}$H$_{22}$N$_3$O$_9$F$_3$: C, 48.74; H, 4.92; N, 8.12; and F, 11.02%. Found: C, 48.67; H, 4.36; N, 7.86; and F, 10.74%.

EXAMPLE III

Standardization of extraction system

Standard solutions ranging between 50 and 500 p.p.m. K$^+$ were prepared by dissolving KCl (99.9% purity) in deionized water. Five milliliter samples of each of the solutions were extracted with 5 ml solutions of 6TF reagent [2×1-$^{-3}$M in CHCl$_3$/TEA(1M)] by adding the organic and aqueous solutions to a test tube and shaking for five minutes. After settling, the aqueous phase was discarded, a 1 ml aliquot of the organic phase transferred to a second test tube, and the solution diluted to 10 ml with CHCl$_3$/TEA (1M).

Figure 2:
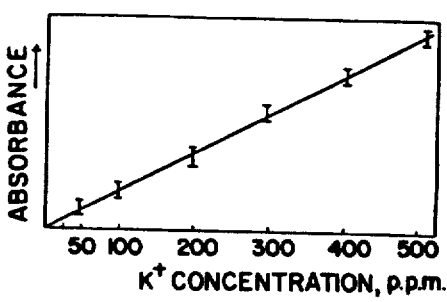
FIG. 2 is a graph showing the increase in absorbance resulting from increases in the level of potassium ion using 4'-(2",4"-dinitro-6"-trifluoromethylphenyl) aminobenzo-15-crown-5.
Figure 3:
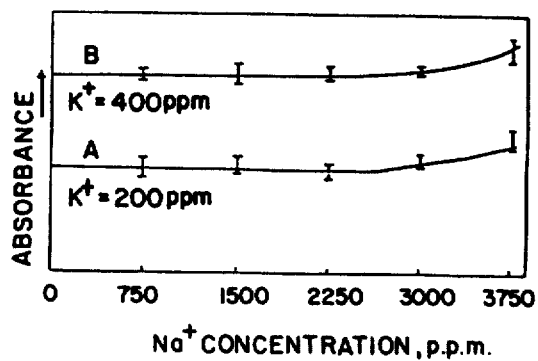
FIG. 3 is a graph showing the effect of sodium ion on the determination of potassium ion at two levels of potassium ion concentration: curve A-200 p.p.m.; curve B-400 p.p.m.

Spectrophotometric measurements were carried out using a Hewlett-Packard 8450 reversed optics spectrophotometer with 10-mm glass cells. The results are summarized in FIG. 2.

EXAMPLE IV

When the procedure of Example III is performed using a solution of 4TF reagent [2×10$^{-3}$ in CHCl$_3$/TEA(1M)] in lieu of 6TF, similar results are obtained.

EXAMPLE V

Determination of extraction constants

In order to determine the extraction constants and the stoichiometry of the 6TF and 4TF reagent compounds, experiments were run in which the pH and the metal concentration were kept constant while the 6TF and 4TF crown ether concentration in the organic phase was varied. With the exception of the reagent concentration, the extraction procedures and test methods employed were similar to those in Example III.

The test results were analyzed and defined in accordance with prior art procedures. [Takagi, et al., *Anal. Lett.*, 1977, 10, 1115; Nakamura et al., *Talanta*, 1978, 26, 921; Nakamura et al., *Anal. Chem.*, 1980, 52, 1668; Pacey et al., *Anal. Lett.*, 1980, 13, 1085]. Table 2 shows the data for the extraction constants.

TABLE 2

EXTRACTION CONSTANTS OF 6TF AND 4'-PICRYLAMINOBENZO-15-CROWN-5
A·1 M TEA buffer solution was used.

| Ion | 6TF | 4'-Picryl-aminobenzyl-15-crown-5 |
|---|---|---|
| $Na^+$ | NA* | ~10 |
| $K^+$ | 7.5 + 0.2 | 7.5 ± 0.2 |
| $Rb^+$ | 8.3 + 0.2 | 8.5 ± 0.2 |
| $Cs^+$ | NA | ~10 |

*NA = no appreciable extraction

The data suggests that the sodium and cesium ions will not interfere with the determination of potassium ion using the 6TF reagent, but that the rubidium ion will. However, the rubidium ion has a very low incidence of natural occurrence.

EXAMPLE VI

A Determination of potassium ion in blood serum

Four samples of human blood serum were labled "A", "B", "C", and "D" and treated as follows.

Each of the serum samples was denatured by admixing 1 ml of the blood serum with 20 ml of 100% ethanol and 2 ml of deionized water. The samples were centrifuged, and the residue discarded.

A solution of $2 \times 10^{-3}$ molar 6TF reagent was prepared by dissolving 1.01 g of 6TF in a liter of organic solvent comprising spectroscopic quality chloroform containing freshly distilled triethylamine in the ratio 1 ml TEA per liter $CHCl_3$.

Five milliliters (5 ml) of this 6TF reagent solution was added to each of the aqueous denatured blood serum samples. The samples were shaken for five minutes, the aqueous and non-aqueous phases permitted to separate, and the aqueous phase discarded.

A pipet was utilized to transfer 1 ml aliquots of the organic phases of each of the samples to test tubes. Each 1 ml aliquot was further diluted with 9 ml of chloroform/TEA (1M), and a portion of the dilute sample transferred to a 10 mm glass cell for spectrophotometric measurements. The measurements were carried out at 480 nm using a Hewlett-Packard 8450 A reversed optics spectrophotometer.

The graphic results of the spectrophotometer analyses were converted to parts per million potassium ion by using the equation:

$$A = (7.62 \pm 0.1) \times 10^{-4} \times [K^+] - (7.04 \pm 3) \times 10^{-4}$$

where A is the absorbance and $[K^+]$ is the concentration of potassium ion in parts per million. The results were compared with determinations made on the human blood serum samples by means of atomic absorption spectroscopy (AAS). The results are tabulated below:

| | P.P.M. $K^+$ in Blood Serum | |
|---|---|---|
| Sample | 6TF | AAS |
| A | 149 | 155 |
| B | 194 | 196 |
| C | 141 | 150 |
| D | 109 | 115 |

EXAMPLE VII

Comparison with Prior Art–Detectability

An experiment was conducted comparing the 6TF reagent of the present invention with a crown ether which the applicants herein reported in the article entitled, "A NEW CHROMOGENIC CROWN ETHER 4"-CYANO-2",6"-DINITRO-4'-AMINOBENZO-15-CROWN-5 AS AN ALKALI METAL EXTRACTION REAGENT", which was published in *ANALYTICAL LETTERS*, 13(A12), 1085–1091 (1980).

The cyano compounds disclosed in the *Analytical Letters* article require buffering at a pH of 11 or 12 in order to achieve a reagent effect. As stated in the article, the only chemicals that can be used to achieve pH values in this range are alkali metal hydroxides: ". . . no amines were available for pH adjustment at that range . . ." (Reference at p. 1089). In the case of blood serum samples, the use of such high pH conditions caused precipitation of other chemical matter in the sample. The resultant turbidity interferes with the spectrophotometric determination and reduces the detectability of the system as shown by the following:

Duplicate 1 ml samples of blood serum were mixed with 2 ml of 100% ethanol and 2 ml of deionized water, resulting in the precipitation of denatured protein. The samples were centrifuged and the residue was discarded. The supernatant portion of each sample was decanted into separatory funnels, and the funnels labeled "A" and "B".

To Sample A was added 5 ml of $2 \times 10^{-3}$M 4'-(2",4"-dinitro-6"-trifluoromethylphenyl) aminobenzo-15-crown-5 (6TF) chloroform reagent prepared by dissolving 1.01 g. of 6TF in a liter of spectroscopic quality chloroform containing distilled triethylamine in the ratio 1 mol TEA per liter of $CHCl_3$. Sample A was shaken for five minutes, the aqueous and non-aqueous phases permitted to separate, and the aqueous phase discarded. A 1 ml aliquot of the organic phase was further diluted with 9 ml of chloroform/TEA and transferred to a 10 mm glass cell for spectrophotometric measurement. The results which were obtained when Sample A was compared with a TEA-buffered reagent blank are similar to those reported in Example VI.

In a similar manner, Sample B was treated by adding 5 ml of $2 \times 10^{-3}$M 4"-cyano-2",6"-dinitro-4'-aminobenzo-15-crown-5 reagent in spectroscopic quality chloroform. The pH of the sample was adjusted to 12.5 by the addition of LiOH. Like Sample A, the sepatory funnel containing Sample B was shaken for 5 minutes. However, it was found that the aqueous and organic phases did not separate (there was a high degree of emulsion). Because of Sample B's high turbidity, spectrophotometric detection was not possible. When the experiment was repeated utilizing CsOH to adjust the pH of the sample, a similar emulsion resulted.

EXAMPLE VIII

Comparison with Prior Art–Accuracy and Reproducibility

As illustrated at Example VI, the reproducibility of an analytical determination for identical samples utilizing the crown ether reagent of the present invention, 4'-(2",4"-dinitro-6"-trifluoromethylphenyl) aminobenzo-15-crown-5 (6TF), is quite high (3-5%), and the accuracy obtained by using the reagent is quite good ($\pm 3$-5% of the sample's actual value). In contrast, poor accuracy and reproducibility were obtained using the cyano crown ether reagent disclosed in the *Analytical Letters* reference (CN) as shown by the following experiment:

Previously analyzed samples of blood serum were adjusted with KCl to form four sets of specimens containing 50, 100, 150 and 200 p.p.m. $K^+$ ion, respectively. Each specimen was treated, employing at least triplicate runs, in accordance with the procedure set forth in Example VII, supra.

The specimens treated with 4"-cyano-2",6"-dinitro-4'-aminobenzo-15-crown-5 (CN) reagent developed a high degree of turbidity. The specimens were centrifuged, allowed to settle overnight and the liquid layer decanted off and spectrophotometrically measured. The results are set forth in the following table:

| Actual value potassium ion | 6TF found | CN found |
|---|---|---|
| 50* | 49 ± 0.5 | 40 ± 5 |
| 100 | 99 ± 1.0 | 80 ± 7 |
| 150 | 151 ± 1.3 | 142 ± 10 |
| 200 | 201 ± 1.5 | 173 ± 9 |

*Values reported are parts per million (p.p.m.) $K^+$ ion in the specimens.

Thus, the 6TF compound of the present invention exhibited significantly greater reproducibility and accuracy than did the CN compound of the reference.

What is claimed:

1. An organic reagent for extracting potassium from an aqueous solution comprising:
   (a) a spectroscopic quality chloroform solvent; and
   (b) the crown ether, 4'-(2",4"-dinitro-6"-trifluoromethylphenyl) aminobenzo-15-crown-5, dissolved in said chloroform solvent, and wherein the concentration of said crown ether in said solvent is in the range $1 \times 10^{-4}$ molar to $1 \times 10^{-2}$ molar.

2. The reagent of claim 1 wherein the concentration of said crown ether in said solvent is approximately $2 \times 10^{-3}$ molar.

3. The reagent of claim 1 further including:
   a base soluble in said chloroform solvent and in a potassium-ion-containing aqueous solution.

4. The reagent of claim 3 wherein said base is selected from the group consisting of tri-i-butylamine, triethylenediamine, isopropylamine, tripropylamine, triethylamine, dimethylamine, di-n-propylamine, and diethylamine.

5. The reagent of claim 3 wherein said base comprises triethylamine.

6. A process for the spectrophotometric determination of the concentration of potassium ions in aqueous solution, said process comprising the following steps:
   (a) mixing in a common vessel a measured quantity of a potassium-ion-containing aqueous solution with a measured quantity of the organic reagent of claim 3, wherein said organic reagent contains a base in sufficient quantity to achieve a pH in said aqueous solution in the range of 9.5 through 11.0 when said organic reagent is admixed therewith;
   (b) agitating said vessel to extract potassium ions from said aqueous solution into said organic reagent;
   (c) transferring a measured quantity of the potassium-ion-containing organic reagent into a spectrophotometric cell;
   (d) detecting absorbance of said potassium-ion-containing organic reagent with the aid of a spectrophotometer with ultraviolet-visible light having wavelength in the range 300 to 700 nm;
   (e) recording the absorbance resulting from said detecting step; and
   (f) comparing said absorbance with a standard calibration curve produced by treating aqueous solutions containing known concentrations of potassium ion in accordance with the procedures of steps a through e.

7. The process of claim 6 wherein the measured quantity of the organic reagent and the measured quantity of the potassium-ion-containing aqueous solution in said common vessel are substantially equal in volume.

8. The process of claim 6 wherein said potassium-ion-containing aqueous solution contains sodium ions.

9. The process of claim 8 wherein the concentration of said sodium ions in said potassium-ion-containing aqueous solution is less than 3000 parts per million.

10. A process for the spectrophotometric determination of the concentration of potassium ions in aqueous solution, said process comprising the following steps:
    (a) adjusting the pH of a potassium-ion-containing aqueous solution with a base to a pH in the range 9.5 through 11.0, said base being substantially free of potassium and rubidium ions, and wherein the amount of sodium ions provided by said base is less than 2000 parts per million;
    (b) mixing in a common vessel a measured quantity of the basic potassium-ion-containing aqueous solution with a measured quantity of the organic reagent of claim 1;
    (c) agitating said vessel to extract potassium ions from said aqueous solution into said organic reagent;
    (d) transfering a measured quantity of the potassium-ion-containing organic reagent into a spectrophotometric cell;
    (e) detecting absorbance of said potassium-ion-containing organic reagent with the aid of a spectrophotometer with ultraviolet-visible light having wavelength in the range 300 to 700 nm;
    (f) recording the absorbance resulting from said detecting step; and
    (g) comparing said absorbance with a standard calibration curve produced by treating aqueous solutions containing known concentrations of potassium ion in accordance with the procedures of steps a through f.

11. The process of claim 10 wherein, in step (a), the pH of the potassium-ion-containing aqueous solution is adjusted with a base to a pH in the range 9.52 10.22.

12. The process of claim 10 wherein said potassium-ion-containing aqueous solution contains sodium ions.

13. The process of claim 12 wherein the concentration of said sodium ions in said potassium-ion-containing aqueous solution is less than 3000 parts per million.

14. The process of claim 12 wherein the measured quantity of the organic reagent solution and the measured quantity of the basic potassium-ion-containing aqueous solution in said common vessel are substantially equal in volume.

15. The process of claim 10 wherein said base comprises a metal hydroxide selected from the group consisting of LiOH and CsOH.

16. The process of claim 15 wherein said base further includes a basic buffer comprising a water soluble salt of a strong base and a weak acid.

17. The process of claim 15 wherein said basic buffer is selected from the group consisting of sodium bicarbonate and borax.

* * * * *

UNITED STATES PATENT AND TRADEMARK OFFICE
CERTIFICATE OF CORRECTION

PATENT NO. : 4,711,853

DATED : December 8, 1987

INVENTOR(S) : PACEY, GILBERT E. and BERNARD P. BUBNIS

Page 1 of 2

It is certified that error appears in the above-identified patent and that said Letters Patent is hereby corrected as shown below:

In the Abstract, line 5, insert a hyphen between the word "crown" and the number "5";

Column 1, line 7, insert a comma after the word "abandoned";

Column 1, line 40, change the hyphen at the end of the line to a closed parenthetical;

Column 1, line 41, delete the closed parenthetical at the beginning of the line;

Column 1, line 59, insert a hyphen between the words "crown" and "like";

Column 2, line 52, change "$2 \times 10^{31}$" to --$2 \times 10^{-4}$--;

Column 2, line 53, change "$_4$M" to --M--;

Column 4, line 24, change "twophase" to --two-phase--;

Column 5, line 63, change "4"nitrobenzo" to --4' nitrobenzo--;

UNITED STATES PATENT AND TRADEMARK OFFICE
CERTIFICATE OF CORRECTION

PATENT NO. : 4,711,853

DATED : December 8, 1987

INVENTOR(S) : PACEY, GILBERT E. and BERNARD P. BUBNIS

It is certified that error appears in the above-identified patent and that said Letters Patent is hereby corrected as shown below:

Column 9, line 56, change "tri-i-butylamine" to --tri-$\underline{i}$-butylamine--;

Column 9, line 58, change "di-n-propylamine" to --di-$\underline{n}$-propylamine--;

Column 10, line 61, between "9.52" and "10.22" insert the word --to--.

Signed and Sealed this

Seventh Day of June, 1988

Attest:

DONALD J. QUIGG

Attesting Officer    Commissioner of Patents and Trademarks